United States Patent [19]

Yurugi et al.

[11] 4,010,265
[45] Mar. 1, 1977

[54] 8-ALKYLPYRIDO[3,4-d]PYRIDAZINES

[75] Inventors: Shojiro Yurugi, Kyoto; Shintaro Kikuchi, Hyogo, both of Japan

[73] Assignee: Takeda Chemical Industries, Ltd., Osaka, Japan

[22] Filed: Mar. 25, 1975

[21] Appl. No.: 562,032

[30] Foreign Application Priority Data

Mar. 28, 1974  Japan .............................. 49-35255

[52] U.S. Cl. ..................... 424/248.4; 260/250 AC; 260/246 B
[51] Int. Cl.² ....................................... C07D 413/14
[58] Field of Search ................ 260/246 B, 250 AC; 424/248, 250

[56] References Cited
OTHER PUBLICATIONS

Shojiro Yurugi et al., Chemical Abstracts vol. 78, 43400h (1973).
Shojiro Yurugi et al., Chemical Abstracts vol. 79, 78,830 W (1973).

*Primary Examiner*—Donald G. Daus
*Assistant Examiner*—Jose Tovar
*Attorney, Agent, or Firm*—Wenderoth, Lind & Ponack

[57] ABSTRACT

Novel 8-alkylpyrido[3,4-d]pyridazines of the formula:

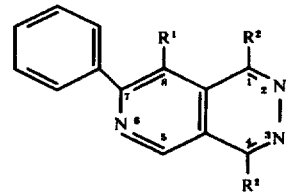

wherein $R^1$ stands for a lower alkyl group; $R^2$ stands for a cyclic amino group, or pharmaceutically acceptable salts thereof, have excellent diuretic activity in mammals including human beings, so that they are useful for therapy for human or animal use.

9 Claims, No Drawings

8-ALKYLPYRIDO[3,4-d]PYRIDAZINES

The present invention relates to novel 8-alkylpyrido-[3,4-d]pyridazines which have effective diuretic action.

There have been synthesized many kinds of diuretics, and some of them have been applied in practice, typical examples of which are chlorothiazide derivatives, acetazolamide, triamterene, trifrocine, furosemide, etc.

However, known diuretics are not very satisfactory in view of one or more disadvantages such as promoting the excretion of potassium as well as sodium, causing side effects (e.g., increase of blood glucose level and blood uric acid level) upon long-term administration, and showing rather low diuretic activity and rather high toxicity.

The present inventors have sought to provide an effective diuretic which is unaccompanied by such disadvantages.

Accordingly, the present inventors have synthesized novel 8-alkylpyrido[3,4-d]pyridazines and have found that these compounds are useful as effective and improved diuretics.

The present invention has been accomplished on the basis of this finding.

Thus, the principal object of the present invention is to provide novel 8-alkylpyrido[3,4-d]pyridazines as well as their salts which are useful as effective and improved diuretics. Another object is to provide an industrially feasible method for the production of these novel compounds.

The 8-alkylpyrido[3,4-d]pyridazines of the present invention are those represented by the following formula:

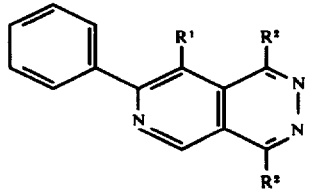

(I)

wherein $R^1$ stands for a lower alkyl group; $R^2$ stands for a cyclic amino group and pharmaceutically acceptable salts thereof.

Referring to the above formulas (I), the lower alkyl group $R^1$ is a straight-chain or branched alkyl group such as, methyl, ethyl, propyl, isopropyl or butyl. The cyclic amino group represented by $R^2$ in general formula (I) is a five- or six-membered cyclic ring containing one or more nitrogen atoms, such as piperidino, pyrrolidino, morpholino or the like, which may be substituted with lower alkyl groups having the same meaning as used in the case of $R^1$. Thus, 2-methylmorpholino, 2,6-dimethylmorpholino, 2,3-dimethylmorpholino, etc. may be mentioned as the example. Furthermore, in pyridazine compound (I), substituents at 1- and 4-positions may differ from each other.

The pharmaceutically acceptable salts of the compound (I) include the corresponding inorganic acid salts such as hydrochloric acid salt, sulfuric acid salt, nitric acid salt, phosphoric acid salt or the like as well as the corresponding organic acid salts such as oxalic acid salt, fumaric acid salt, tartaric acid salt, malic acid salt, trifluoroacetic acid salt, or the like.

The compound of the general formula (I) or its pharmaceutically acceptable salt is prepared by per se known methods, such as the methods described in Dutch Patent Application No. 7217773. A preferable method is the method which comprises reacting a compound of the formula:

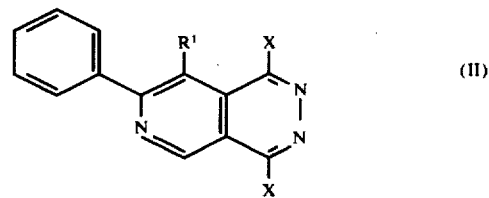

(II)

wherein $R^1$ has the meaning defined above; X stands for halogen, with a cyclic amine corresponding to the cyclic amino group represented by $R^2$ of the compound (I).

The halogen represented by X may for example by chlorine, bromine or iodine.

While this reaction of compound (II) with the cyclic amine proceeds even in the absence of a solvent, the use of a suitable solvent may allow the reaction to proceed more smoothly. The solvent used for this reaction may be any solvent which does not affect the reaction and is exemplified by alcohols such as methanol, ethanol, etc.; ethers such as tetrahydrofuran, ethyl ether, etc.; hydrocarbons and halogenated hydrocarbons such as benzene, chloroform, etc.; and esters such as ethyl acetate. As for the amount of said cyclic amine, to each mole of the starting material of general formula (II), about 2 to 4 moles are employed so that said amine will also function as the reaction solvent and acid acceptor as well. There are no particular limits on the conditions of reaction including the temperature and time. Thus, while the reaction proceeds even at room temperature, it may be accelerated by heating the reaction system to a temperature up to the boiling point of the solvent used or of the cyclic amine. The reaction time is commonly 1 to 5 hours, although it varies with different starting materials, solvents and other factors. The contemplated compound, thus obtained, of general formula (I) may be recovered and purified by conventional treatments such as extraction with a suitable solvent (e.g., water, ethyl acetate, benzene, chloroform, ethanol, etc.), recrystallization, column chromatography and so on. Or, the objective compound may be recovered in the form of acid addition salt as mentioned above, through a per se known conventional manner.

The starting compound (II) used in the above method can be prepared by per se known methods, e.g., the methods described in Dutch Patent Application No. 7217773, some of which are illustrated in the following scheme:

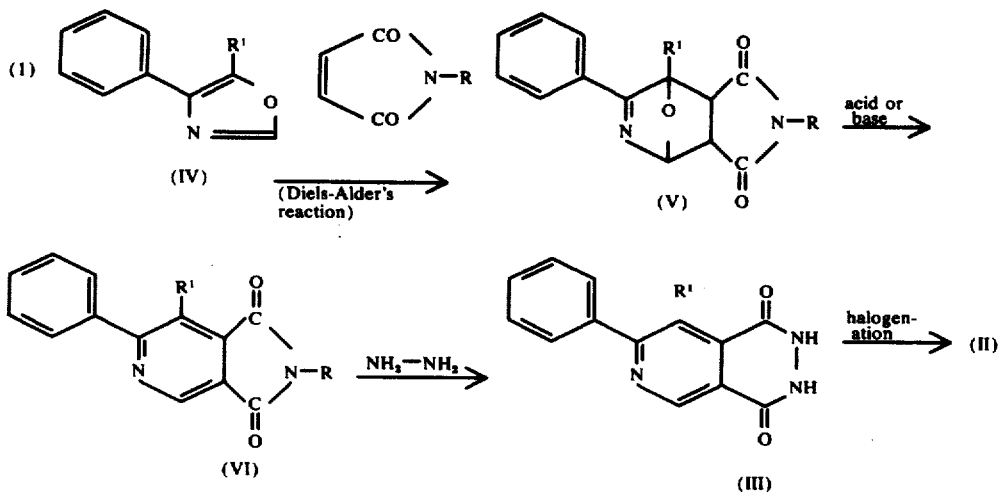

($R^1$ has the meaning defined hereinbefore; R stands for an aliphatic group or an aromatic group)

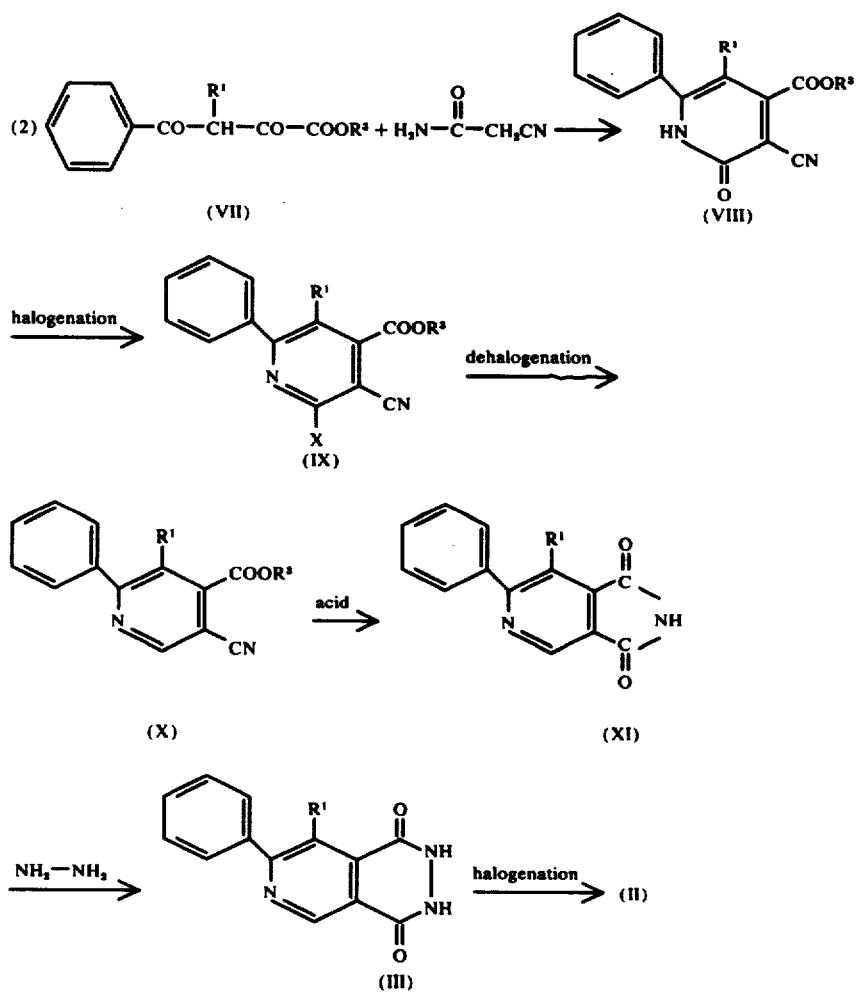

($R^1$ and X have the meaning defined hereinbefore; $R^3$ stands for a lower alkyl group)

The contemplated compounds (I) as well as pharmaceutically acceptable salts thereof, which can be produced in the above manner, have excellent diuretic activity in mammals including human beings and are of value as diuretics. In more detail, the present compounds have the following properties:

1. The compounds of this invention have effective and strong diuretic action.

2. They show extremely low toxicity.

3. They induce urinary excretion of a large amount of sodium ion, but induce urinary excretion of a relatively small amount of potassium ion which is an essential element to the human body. Thus, the excretion ratio of urinary $Na^+/K^+$ is comparatively high in the present compounds.

4. The present compounds can produce a marked additional diuretic response in the animal undergoing maximum diuresis with known diuretics. This fact suggests that the mechanism of diuretic action of the present compounds is different from those of known diuretics. Thus, the combination of the present compounds with other known diuretics can produce much increased diuretic effect.

Therefore, the compounds of the present invention can be used as diuretics for treating ascites including congestive heart failure, liver cirrhosis, hypertension, nephritis, uremia, etc. This may be achieved by using the compound alone or in the form of a pharmaceutically acceptable composition in admixture with a suitable and conventional carrier or adjuvant. The pharmaceutical composition may take the form of tablets, granules, powders, capsules, injections and may be administered orally or parenterally. Usual daily doses of the compounds lie in the range of about 2 to about 200 milligrams per human adult upon oral administration or of about 5 to 50 milligrams parenteral administration. Some examples of practical formulation in which compound (I) of this invention is utilized as a remedy for congestive heart failure, liver cirrhosis, hypertension or nephritis, are as follows:

| | | |
|---|---|---|
| (1) | 8-methyl-1,4-dimorpholino-7-phenylpyrido[3,4-d]-pyridazine | 50 mg. |
| | | 50 mg./capsule |
| (2) | 8-methyl-1,4-dimorpholino-7-phenylpyrido[3,4-d]-pyridazine | 50 mg. |
| | lactose | 50 mg. |
| | | 100 mg./capsule |
| (3) | 8-methyl-1,4-bis-(2-methylmorpholino)-7-phenylpyrido[3,4-d]pyridazine | 50 mg. |
| | corn starch | 50 mg. |
| | | 100 mg./capsule |

It is to be understood that the following examples are presented solely for the purpose of illustration and are not to be construed as limitations of this invention. Many variations of these examples may be resorted to without departing from the spirit and scope of this invention. In this specification, "g.", "mg." and "calcd.", are "gram", "milligram" and "calculated", respectively.

THE PREPARATION OF THE STARTING COMPOUND (II)

1. 1,4-dichloro-8-methyl-7-phenylpyrido[3,4-d]pyridazine

In 100 ml. of toluene, 10 g. of 5-methyl-4-phenyloxazole and 11 g. of N-phenylmaleinimide were boiled on reflux for 16 hours, after which the toluene was distilled off. To the residue was added 50 ml. of ethyl ether and the resultant crystals were recovered by filtration. The procedure yielded 9 g. of 4-methyl-3,N-diphenyl-7-oxa-2-azabicyclo[2,2,1]-hept-2-ene-5,6-carboximide melting at 144°–145° C.

Elemental analysis, for $C_{20}H_{16}O_3N_2$, Calcd. C, 72.28; H, 4.85; N, 8.43, Found C, 72.30; H, 4.70; N, 8.35.

In 80 ml. of dioxane was dissolved 8.7 g. of 4-methyl-3,N-diphenyl-7-oxa-2-azabicyclo[2,2,1]hept-2-ene-5,6-carboximide, followed by the addition of 0.3 ml. of concentrated hydrochloric acid. The mixture was heated at 80° C for 1 hour and the resultant crystals were recrystallized from ethanol. The procedure yielded 5.7 g. of 3-methyl-2,N-diphenylpyridine-4,5-carboximide melting at 204°–205° C.

Elemental analysis, for $C_{20}H_{14}O_2N_2$, Calcd. C, 76.42; H, 4.49; N, 8.91, Found C, 76.59; H, 4.31; N, 8.94.

Together with 3.7 g. of hydrazine hydrate and 27 ml. of glacial acetic acid, 3.7 g. of 3-methyl-2,N-diphenyl-pyridine-4,5-carboximide was boiled on reflux for 1 hour. After cooling, the resultant crystals were recovered by filtration, washed with water and dried. The procedure yielded 2.5 g. of 8-methyl-7-phenyl-1,2,3,4-tetrahydropyrido[3,4-d]pyridazine-1,4-dione melting at 300° C or up.

Elemental analysis, for $C_{14}H_{11}O_2N_3$, Calcd. C, 66.39; H, 4.38; N, 16.59, Found C, 65.82; H, 4.29; N, 16.78.

A mixture of 350 mg. of 8-methyl-7-phenyl-1,2,3,4-tetrahydropyrido[3,4-d]pyridazine-1,4-dione, 0.4 g. of α-picoline and 4 ml. of phosphorus oxychloride was heated at 120° C for 1 hour and, then, concentrated to dryness under reduced pressure. To the residue was added ice-water and the resultant crystals were recovered by filtration, whereby 1,4-dichloro-8-methyl-7-phenylpyrido[3,4-d]pyridazine was obtained. Recrystallization from benzene yielded 310 mg. of colorless needles melting at 143°–144° C.

Elemental analysis, for $C_{14}H_9N_2Cl_2$, Calcd. C, 61.00; H, 3.28; N, 10.12, Found C, 60.87; H, 3.31; N, 9.98.

2. 1,4-dichloro-8-ethyl-7-phenylpyrido[3,4-d]pyridazine

In a procedure similar to (1), 11 g. of 5-ethyl-4-phenyloxazole is used instead of 5-methyl-4-phenyloxazole, whereby 3.2 g. of the above-indicated compound is obtained.

3. 8-benzyl-1,4-dichloro-7-phenylpyrido[3,4-d]pyridazine

In a procedure similar to (1), 13 g. of 5-benzyl-4-phenyloxazole is used instead of 5-methyl-4-phenylaxazole, whereby 3.0 g. of the above-indicated compound is obtained.

EXAMPLE 1

A mixture of 300 mg. of the 1,4-dichloro-8-methyl-7-phenylpyrido[3,4-d]pyridazine and 7 g. of morpholine was heated at 120° C for 1.5 hours and the excess morpholine was distilled off. To the residue was added 10 ml. of water and the crystals were recovered by filtration, washed with water and dried. Recrystallization from a mixture of ethyl ether and ethanol yielded 230 mg. of 8-methyl-1,4-dimorpholino-7-phenylpyrido[3,4-d]pyridazine melting at 187°–189° C.

Elemental analysis, for $C_{22}H_{25}O_2N_5$, Calcd. C, 67.50; H, 6.44; N, 17.89, Found C, 67.24; H, 6.48; N, 17.31.

EXAMPLE 2

2.8 g. of 1,4-dichloro-8-ethyl-7-phenylpyrido[3,4-d]pyridazine was heated together with 40 g. of morpholine at 120° C for 1.5 hours, after which time the excess morpholine was distilled off. To the residue was added 60 ml. of water and the resultant crystals were recovered by filtration, washed with water, dried and recrystallized from ethanol. The described procedure yielded 2.25 g. of 8-ethyl-1,4-dimorpholino-7-phenyl-pyrido[3,4-d]pyridazine melting at 197°-198° C.

Elemental analysis, for $C_{23}H_{27}O_2N_5$, Calcd. C, 68.12; H, 6.71; N, 17.27, Found C, 67.80; H, 6.75; N, 17.05.

EXAMPLE 3

3.0 g. of 1,4-dichloro-8-ethyl-7-phenylpyrido[3,4-d]-pyridazine was heated together with 15 g. of piperidine at 120° C for 1.5 hours, after which time the excess piperidine was distilled off. To the residue was added 60 ml. of water and the resultant crystals were recovered by filtration and were chromatographed on a column packed with silica gel, followed by elution with a mixed solvent of acetone-benzene (1:8). The combined eluate is concentrated and the residue was dissolved in 100 ml. of ethanol. Following the addition of 5 ml. of water, the solution was concentrated to dryness. The concentrate was diluted with 100 ml. of water and stirred, whereupon 2.5 g. of 8-ethyl-7-phenyl-1,4-dipiperidinopyrido-[3,4-d]pyridazine was obtained. Melting point: 64°-65° C.

Elemental analysis, for $C_{25}H_{31}N_5 \cdot \frac{1}{2}H_2O$, Calcd. C, 73.13; H, 7.87; N, 17.06, Found C, 73.03; H, 7.66; N, 16.90.

EXAMPLE 4

8.00 mg. of 1,4-dichloro-8-methyl-7-phenyl-pyrido[3,4-d]pyridazine was heated together with 2 g. of 2-methyl-morpholine at 120° C for 1.5 hours, after which time the excess 2-methylmorpholine was distilled off. To the residue was added 30 ml. of water and the resultant crystals were recovered by filtration and purified by column chromatography (silica gel; acetone: benzene=1:8) in the same manner described in Example 3. After removal of the solvent, the residue was dissolved in 20 ml. of ethanol. Following the addition of 2 ml. of water, the solution was concentrated to dryness. To the residue was added 20 ml. of water, followed by stirring. The resultant crystals were dried in a vacuum dryer at 50°-60° C for 12 hours, whereupon 600 mg. of 8-methyl-1,4-bis(2-methylmorpholino)-7-phenylpyrido-[3,4-d]pyridazine was obtained. Melting point: 96°-99° C.

Elemental analysis, for $C_{24}H_{30}O_2N_5$, Calcd. C, 68.71; H, 6.97; N, 16.70, Found C, 68.14; H, 6.95; N, 16.48.

EXAMPLE 5

650 mg. of 8-benzyl-1,4-dichloro-7-phenyl-pyrido[3,4-d] pyridazine was heated together with 10 g. of morpholine at 140° C for 4 hours and the excess morpholine was distilled off. To the residue was added 20 ml. of water and the crystals were recovered by filtration, washed with water and dried. Recrystallization from methanol yielded 520 mg. of 8-benzyl-1,4-dimorpholino-7-phenylpyrido[3,4-d]pyridazine melting at 185°-187° C.

Elemental analysis, for $C_{28}H_{29}O_2N_5$, Calcd. C, 71.92; H, 6.25; N, 14.98, Found C, 71.92; H, 6.03; N, 15.02.

What is claimed is:

1. A pyrido[3,4-d]pyridazine of the formula:

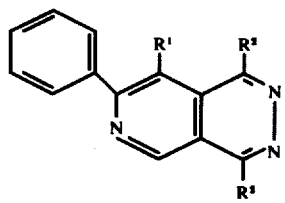

wherein $R^1$ stands for methyl or ethyl, $R^2$ stands for pyrrolidino, morpholino, methyl-morpholino, ethyl-morpholino, piperidino, methyl-piperidino or ethyl-piperidino, or a pharmaceutically acceptable acid salt thereof.

2. A pyrido[3,4-d]pyridazine as claimed in claim 1 wherein $R^2$ is morpholino.

3. A pyrido[3,4-cl]pyridazine as claimed in claim 2, which is 8-methyl-1,4-dimorpholino-7-phenylpyrido-[3,4-d]pyridazine.

4. A pyrido[3,4-d]pyridazine as claimed in claim 2, which is 8-ethyl-1,4-dimorpholino-7-phenylpyrido-[-phenylpyrido-[3,4-d]pyridazine.

5. A pyrido[3,4-d]pyridazine as claimed in claim 1, wherein $R^2$ is methyl-morpholino or ethyl-morpholino.

6. A pyrido[3,4-d]pyridazine as claimed in claim 5, which is 8-methyl-1,4-bis-(2-methylmorpholino)-7-phenylpyrido[3,4-d]pyridazine.

7. A pyrido[3,4-d]pyridazine as claimed in claim 1 wherein $R^2$ is methyl-piperidino or ethyl-piperidino.

8. A pyrido[3,4-d]pyridazine as claimed in claim 7, which is 8-ethyl-1,4-dipiperidino-7-phenylpyrido-[3,4-d]pyridazine.

9. A method of treating ascites which consists essentially of administering to a patient suffering therefrom a medicinally effective amount of a compound of claim 1.

* * * * *